United States Patent
Hatta

(10) Patent No.: US 10,226,308 B2
(45) Date of Patent: Mar. 12, 2019

(54) METHOD OF CONTROLLING A MEDICAL MASTER/SLAVE SYSTEM

(71) Applicant: OLYMPUS CORPORATION, Tokyo (JP)

(72) Inventor: Izumi Hatta, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 169 days.

(21) Appl. No.: 15/003,967

(22) Filed: Jan. 22, 2016

(65) Prior Publication Data
US 2016/0135910 A1 May 19, 2016

Related U.S. Application Data

(63) Continuation of application No. PCT/JP2014/066012, filed on Jun. 17, 2014.

(30) Foreign Application Priority Data

Jul. 24, 2013 (JP) .................................. 2013-153266

(51) Int. Cl.
*G06F 19/00* (2018.01)
*A61B 34/37* (2016.01)
(Continued)

(52) U.S. Cl.
CPC .............. *A61B 34/37* (2016.02); *A61B 34/30* (2016.02); *A61B 34/74* (2016.02); *A61B 2034/301* (2016.02)

(58) Field of Classification Search
CPC ......... A61B 34/37; A61B 34/30; A61B 34/74; A61B 2034/301; B25J 9/1676
(Continued)

(56) References Cited

U.S. PATENT DOCUMENTS

2003/0046401 A1* 3/2003 Abbott ................. G06F 9/4443
709/228
2004/0243147 A1 12/2004 Lipow
(Continued)

FOREIGN PATENT DOCUMENTS

CN 1728972 A 2/2006
CN 100389730 C 5/2008
(Continued)

OTHER PUBLICATIONS

Extended Supplementary European Search Report dated May 10, 2017 in European Patent Application No. 14 82 8871.5.
(Continued)

*Primary Examiner* — Ronnie M Mancho
(74) *Attorney, Agent, or Firm* — Scully, Scott, Murphy & Presser, P.C.

(57) ABSTRACT

A method of controlling the medical master/slave system comprising a bendable master apparatus operated by an operator and a slave apparatus inserted through the body. The control method includes an ordinary actuation mode (Step S101) in which, based on a bending state of the master apparatus, the slave apparatus is actuated in such a way as to become similar in operation to the master apparatus, a reversal actuation mode (Step S105) in which, based on a bending state of the master apparatus, the slave apparatus is actuated in such a way as to be reversed relative to the operation of the master apparatus, and a transition mode (Step S103, S104, S107, S108) for transition between the ordinary actuation mode and the reversal actuation mode.

13 Claims, 11 Drawing Sheets

(51) Int. Cl.
*A61B 34/30* (2016.01)
*A61B 34/00* (2016.01)

(58) Field of Classification Search
USPC .......................................................... 700/245
See application file for complete search history.

(56) References Cited

U.S. PATENT DOCUMENTS

| | | | |
|---|---|---|---|
| 2004/0254680 A1 | 12/2004 | Sunaoshi | |
| 2005/0166413 A1* | 8/2005 | Crampton | B25J 13/088 33/503 |
| 2006/0178556 A1 | 8/2006 | Hasser et al. | |
| 2007/0135803 A1* | 6/2007 | Belson | A61B 1/00154 606/1 |
| 2009/0326553 A1 | 12/2009 | Mustufa et al. | |
| 2011/0245661 A1 | 10/2011 | Yoshie et al. | |
| 2011/0288573 A1* | 11/2011 | Yates | A61B 17/07207 606/170 |
| 2011/0295269 A1* | 12/2011 | Swensgard | A61B 17/068 606/130 |
| 2011/0295270 A1* | 12/2011 | Giordano | A61B 17/00234 606/130 |
| 2012/0078053 A1 | 3/2012 | Phee et al. | |
| 2013/0079594 A1 | 3/2013 | Motoki | |
| 2014/0200407 A1 | 7/2014 | Donhowe et al. | |

FOREIGN PATENT DOCUMENTS

| | | |
|---|---|---|
| CN | 102076276 A | 5/2011 |
| CN | 102596064 A | 7/2012 |
| CN | 102711586 A | 10/2012 |
| CN | 102802551 A | 11/2012 |
| JP | H05-076482 A | 3/1993 |
| JP | H05-154782 | 6/1993 |
| JP | H07-328016 A | 12/1995 |
| JP | H08-224248 A | 9/1996 |
| JP | 3339953 B2 | 10/2002 |
| JP | 2007-175502 A | 7/2007 |
| JP | 4608601 B2 | 1/2011 |
| JP | 2013-066617 A | 4/2013 |
| WO | 2004/052171 A3 | 6/2004 |
| WO | WO 2010/055745 A1 | 5/2010 |

OTHER PUBLICATIONS

International Search Report dated Sep. 16, 2014 issued in PCT/JP2014/066012.

\* cited by examiner

[Fig.1]
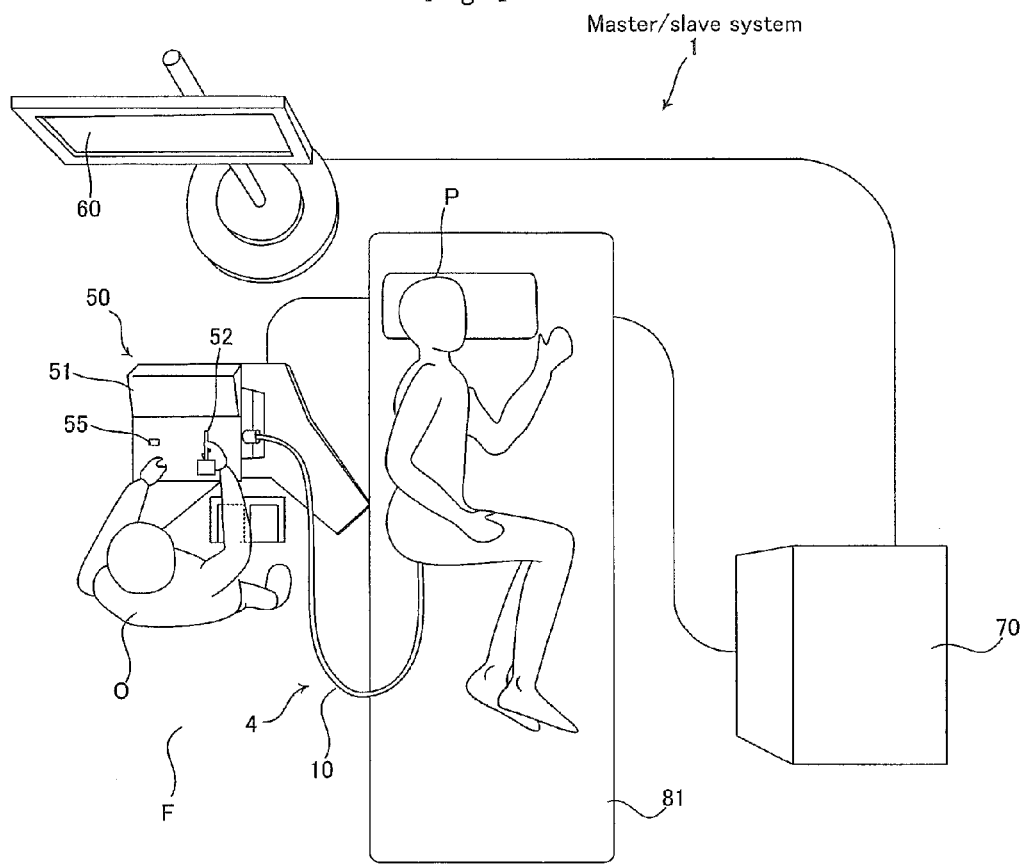
[Fig.2]
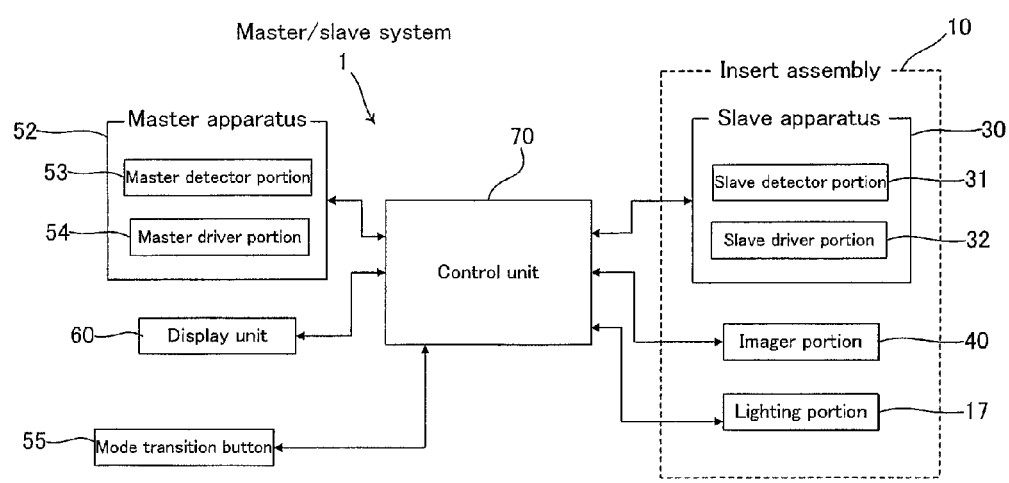

[Fig.3]
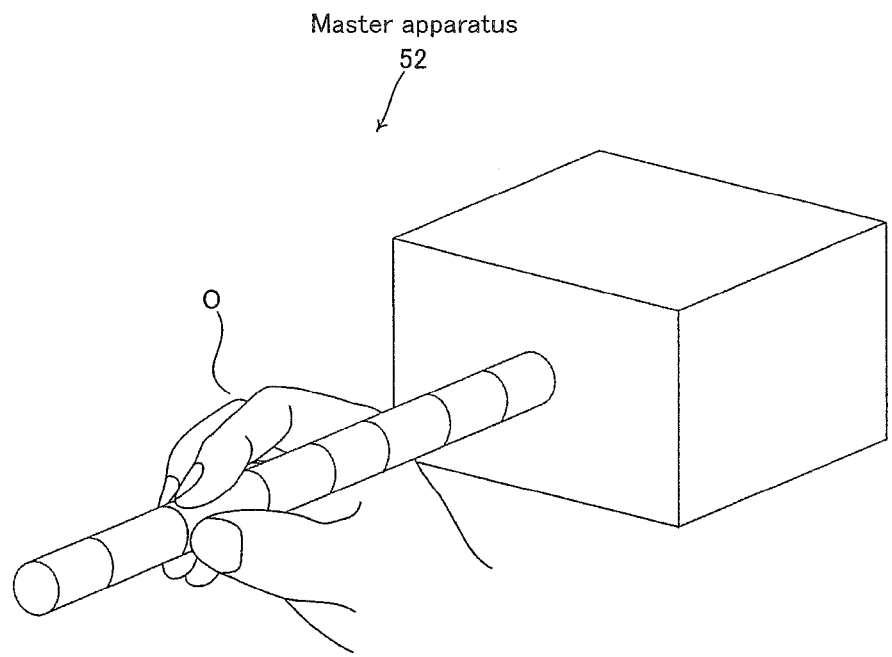
[Fig.4]
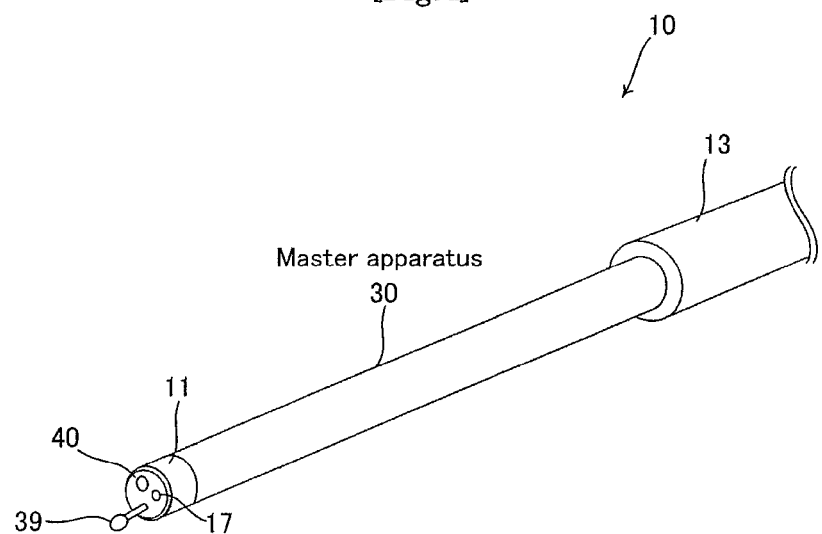

[Fig.5]
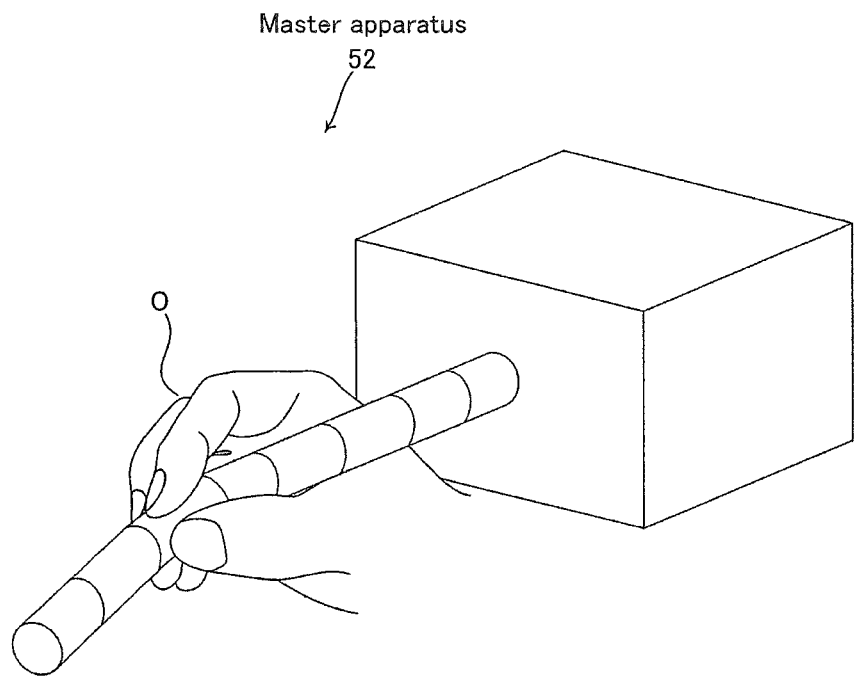
[Fig.6]
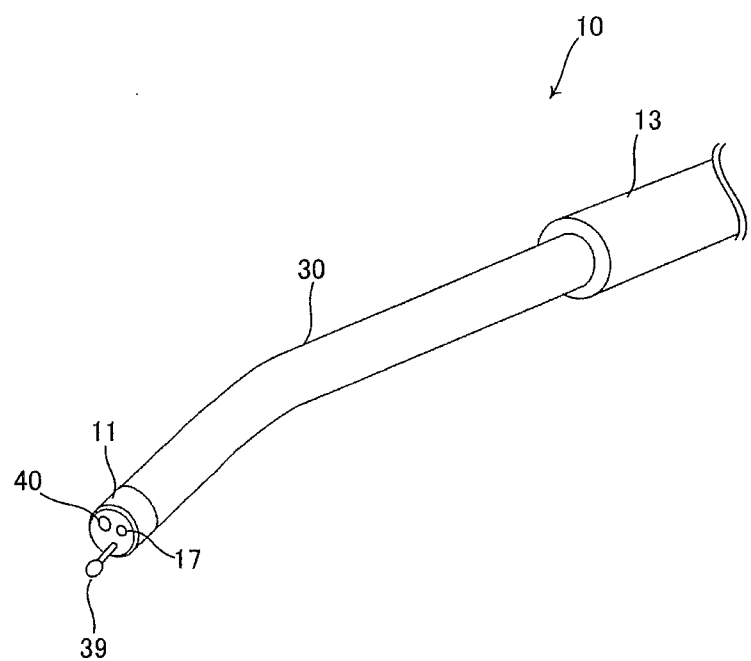

[Fig.7]
Master apparatus
52
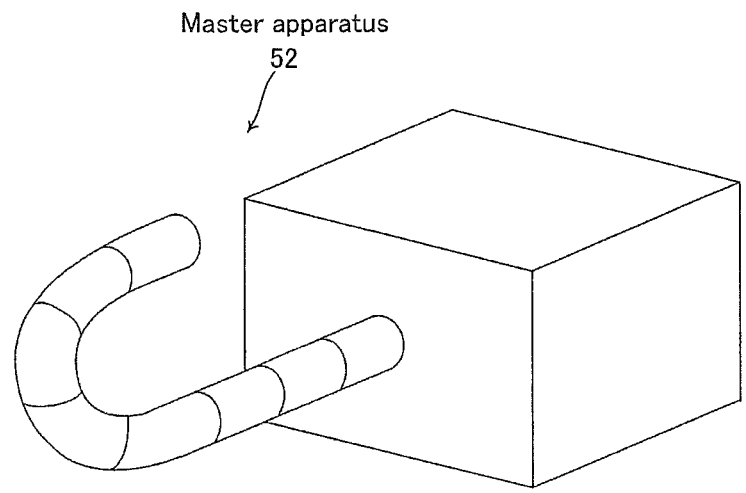
[Fig.8]
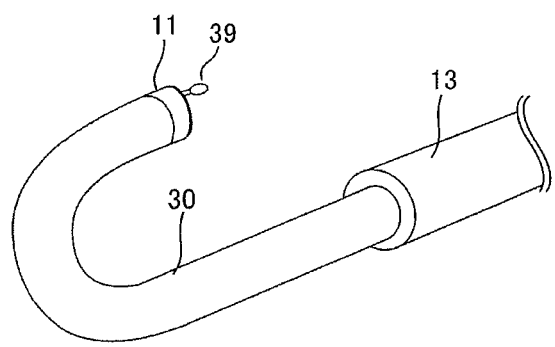

[Fig.9]
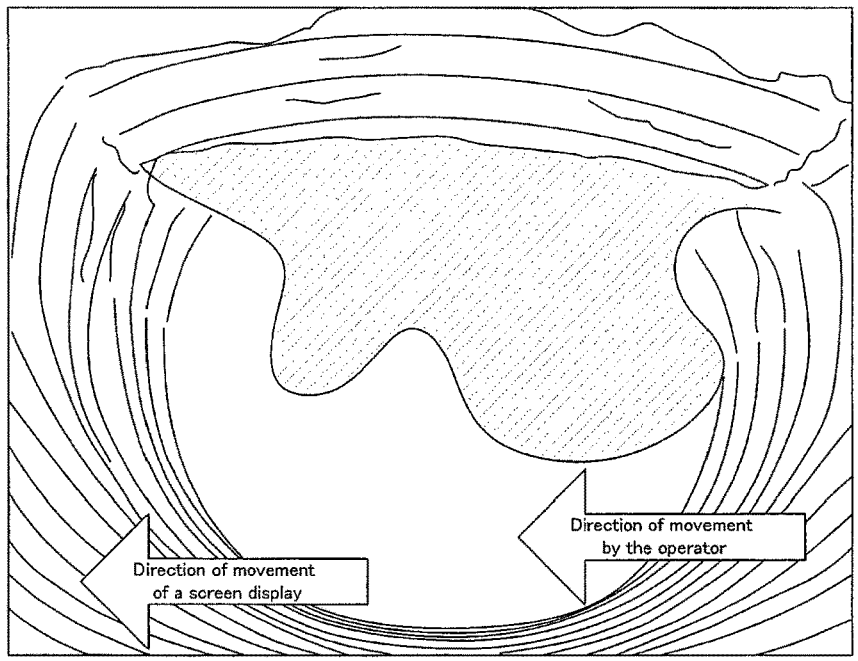
[Fig.10]
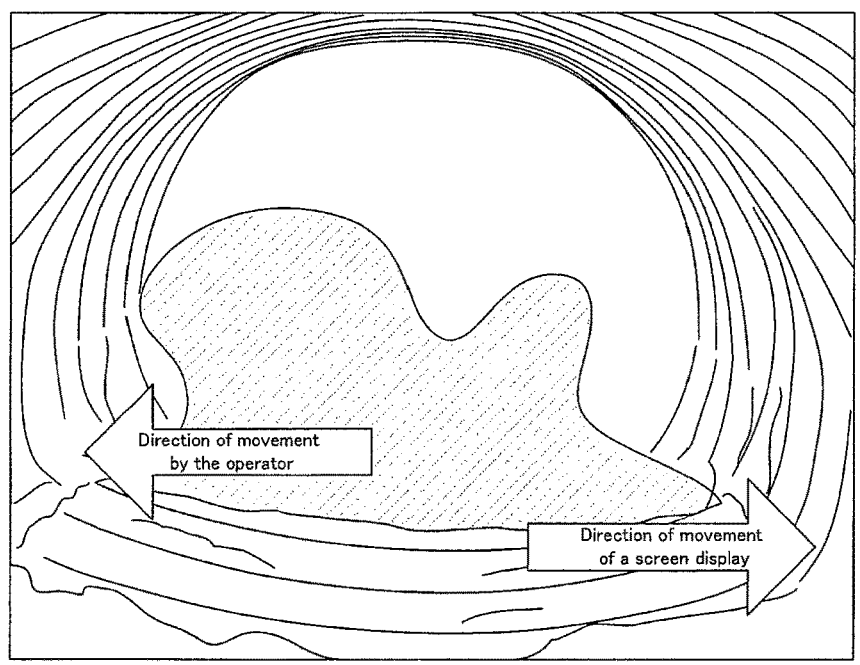

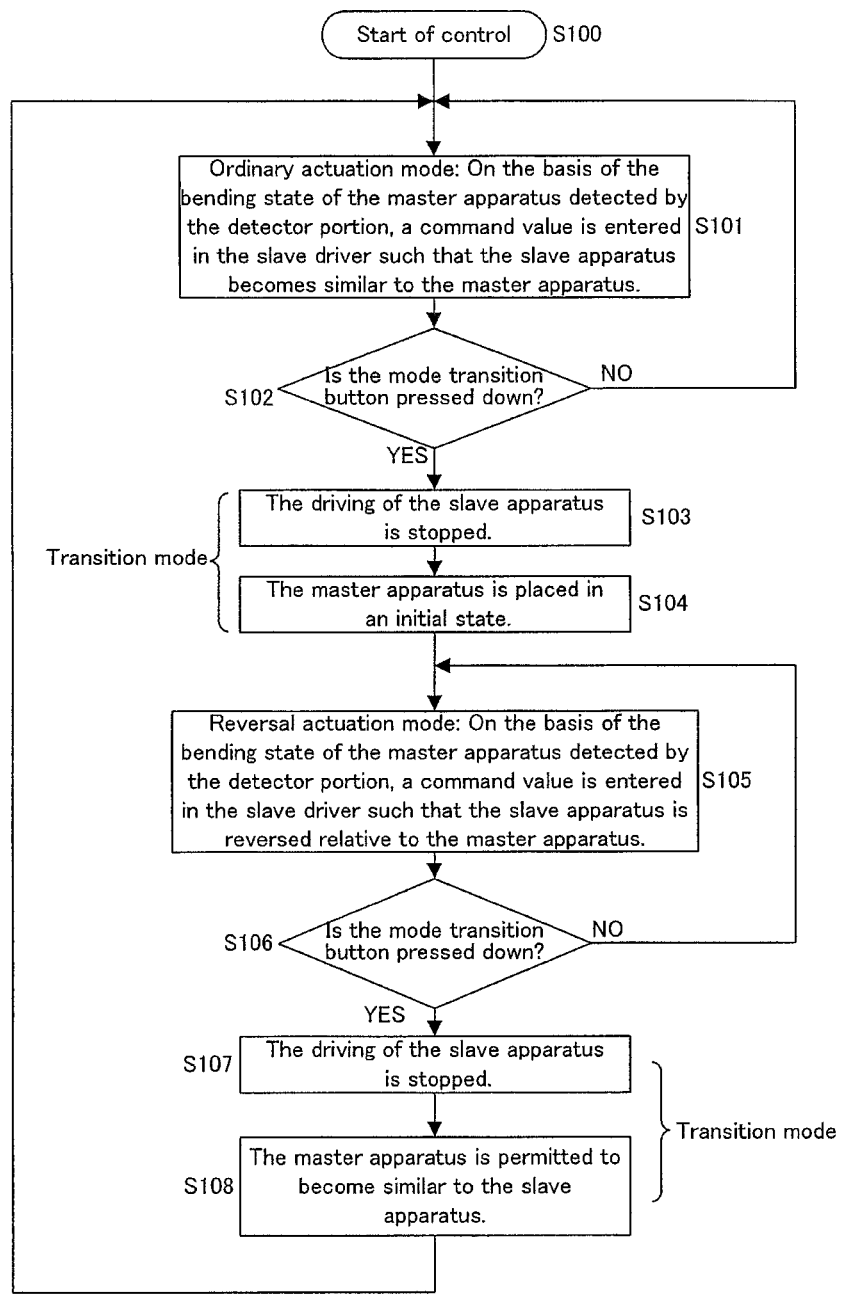
[Fig.11]
Manual changeover

[Fig.12]
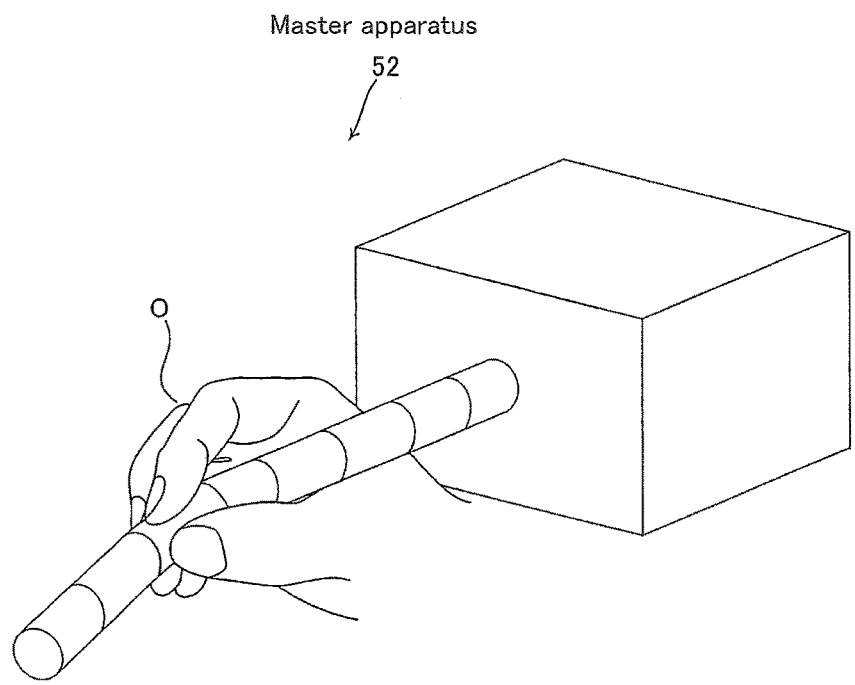
Operation during the reversal actuation mode
[Fig.13]
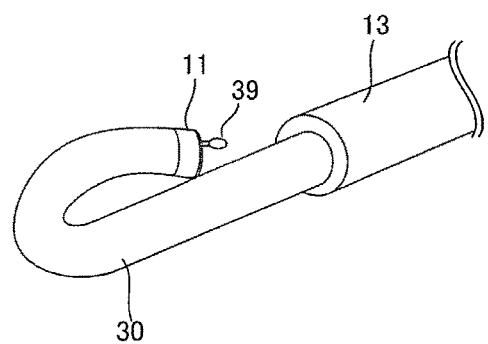
Figure illustrative of interference

[Fig.14]
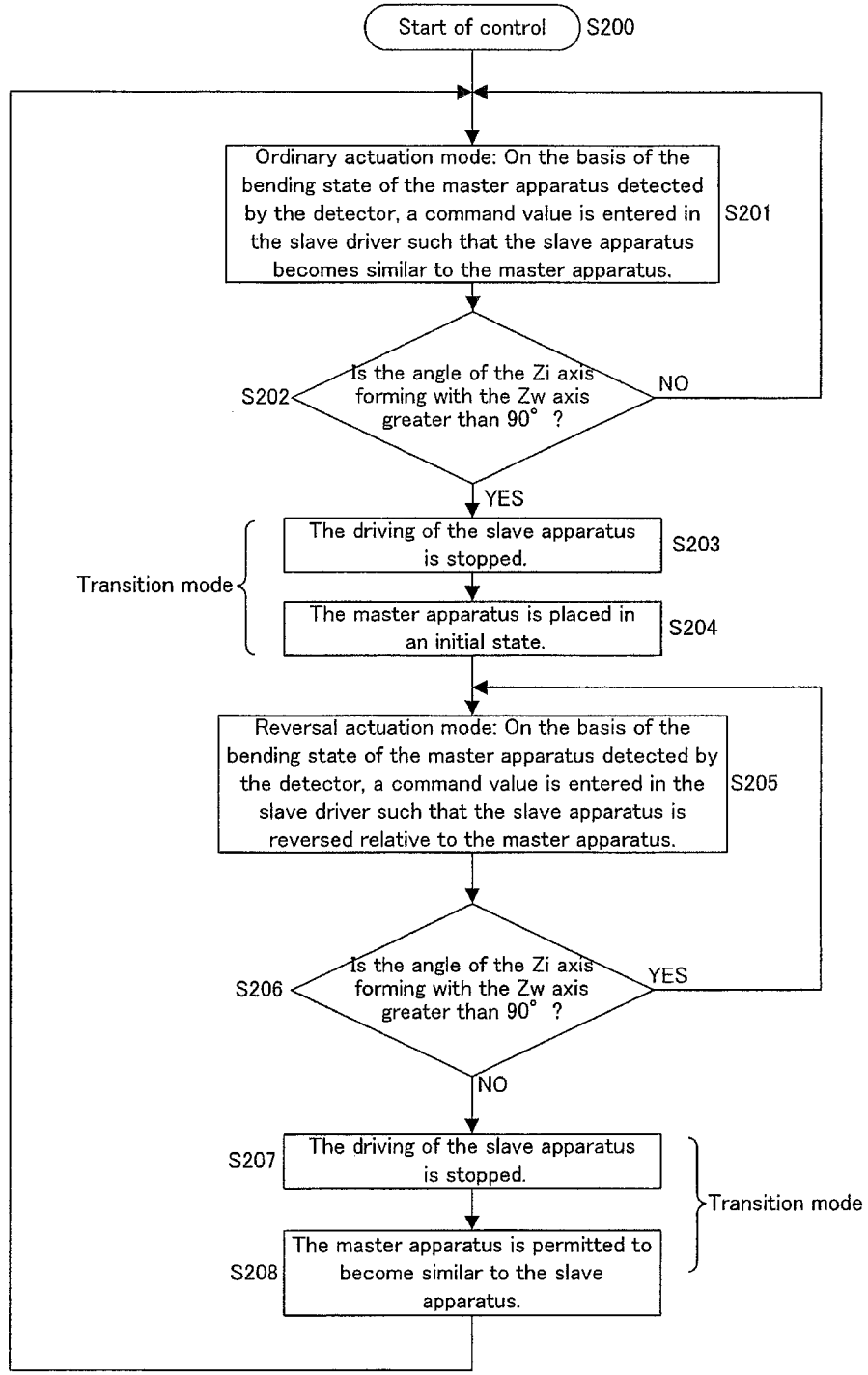
Automatic changeover

[Fig.15]
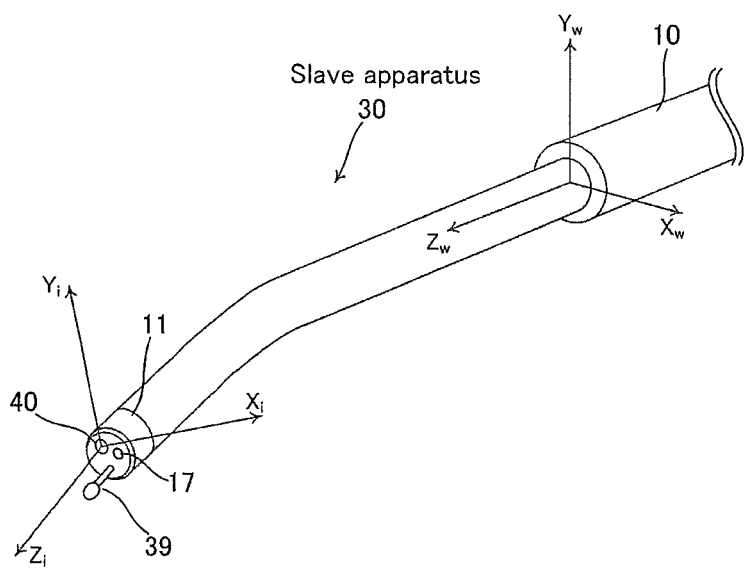

[Fig.16]
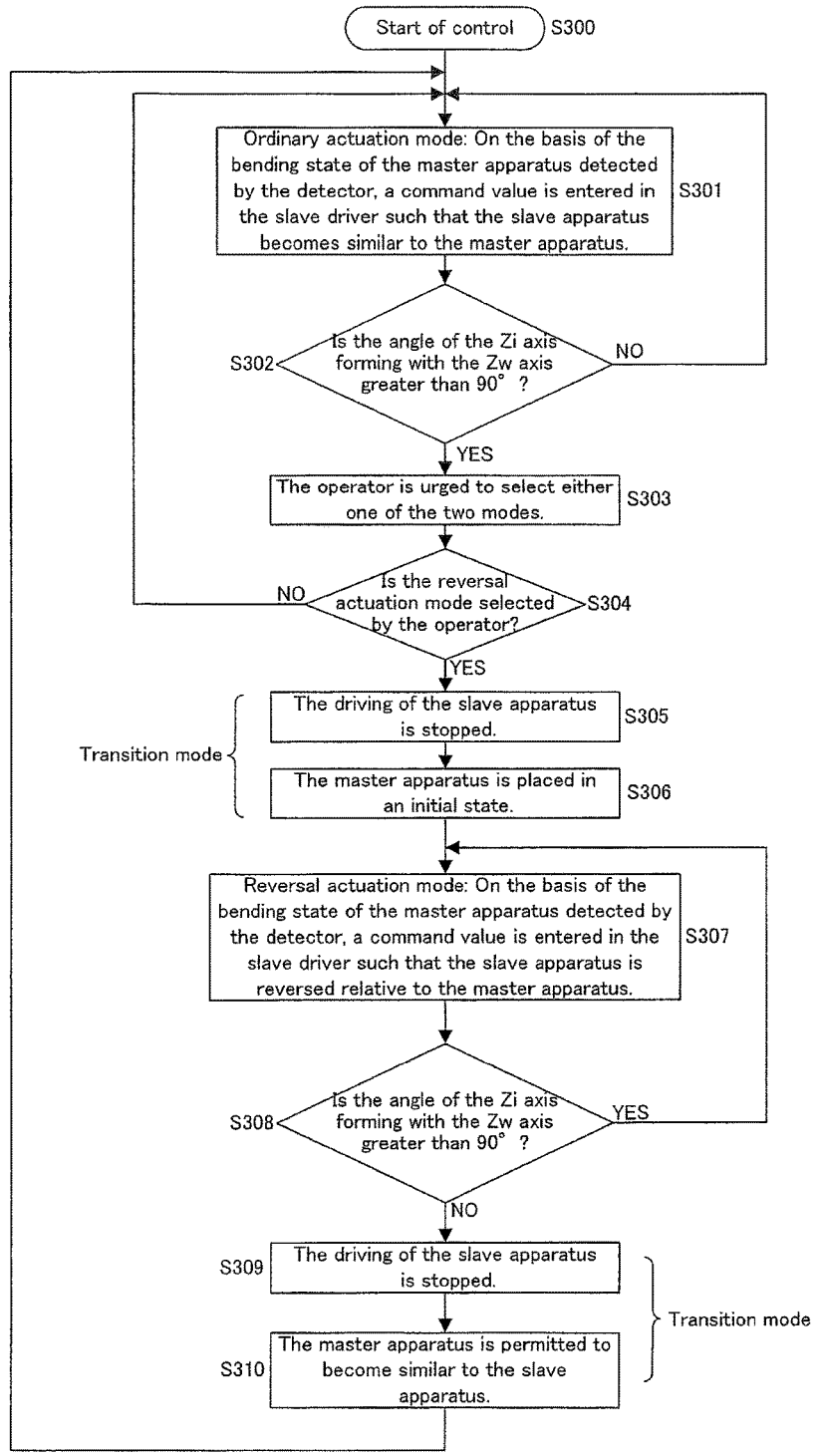
After notified to the operator, the operator makes a selective changeover.

[Fig.17]
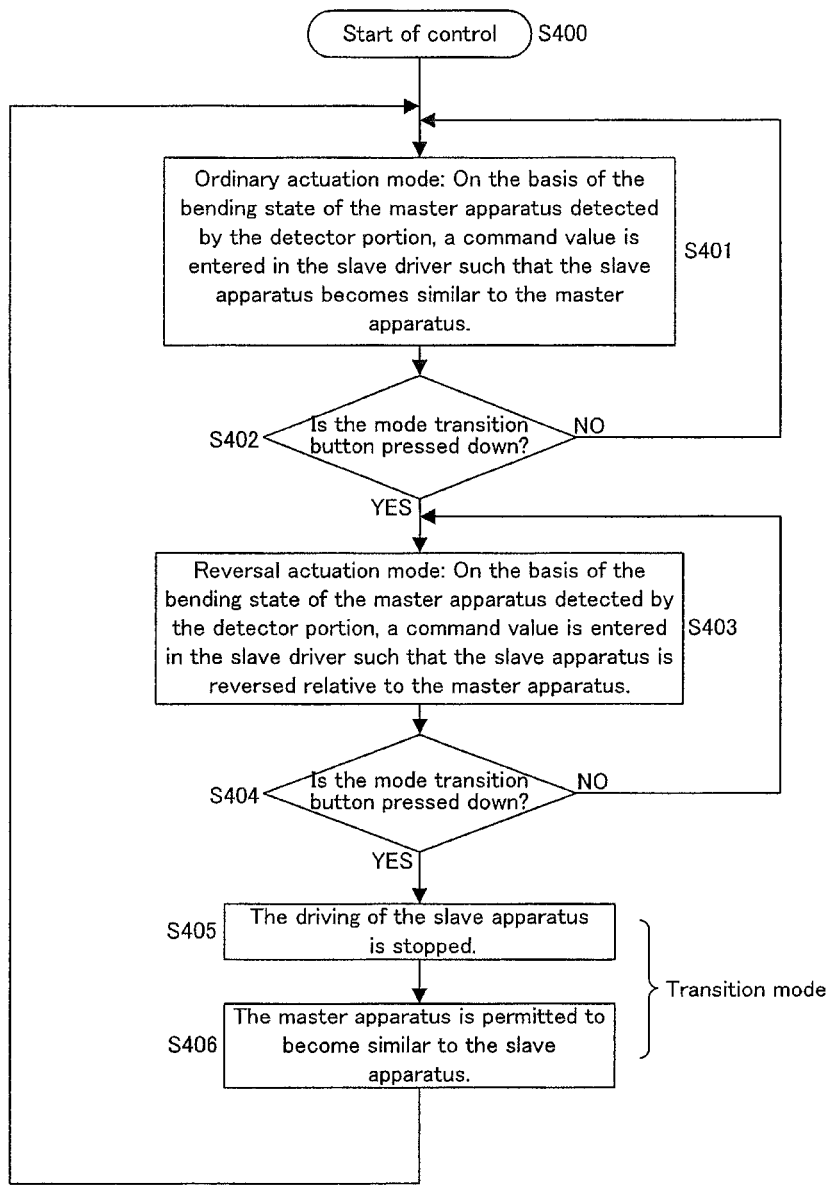

METHOD OF CONTROLLING A MEDICAL MASTER/SLAVE SYSTEM

CROSS-REFERENCES TO RELATED APPLICATIONS

This application is a Continuation Application of International Application PCT/JP2014/066012 filed on Jun. 17, 2014, which claims priority to Japanese Patent Application No. 2013-153266 filed on Jul. 24, 2013. The Contents of International Application PCT/JP2014/066012 and Japanese Patent application No. 2013-153266 are hereby incorporated by reference herein in its entirety.

BACKGROUND OF THE INVENTION AND RELATED ART STATEMENT

The present invention relates to a method of controlling a medical master/slave system that is used while inserted through the body cavity to apply treatments to various in-vivo tissues.

So far there has been a master/slave system known as a surgery support system comprising a master manipulator operated by an operator and a slave manipulator for performing treatments on the basis of actuation of the master manipulator.

There is endoscopic mucosal resection now available wherein such a surgical robot is used to insert the slave manipulator through the body cavity to cut off affected sites on mucosal tissues by means of a treatment tool. Such surgical operation is expected to have a wider range of applications because there is no need for abdominal operation, resulting in limited burdens on patients and some consideration curtailments in the number of days taken until postoperative recuperation and leaving hospital.

Typically for an endoscopic operation system for performing such operation, Japanese Patent No. 4608601 discloses a medical system characterized by comprising an insert slave apparatus that is inserted through the body and includes a bendable first bending portion and a bendable second bending portion located on a proximal end side of said first bending portion, a treatment slave apparatus that is inserted together with said insert slave apparatus and used in combination with said insert slave apparatus to apply treatments to sites under operation, an insert master portion that includes a movable portion, a rotatable first joint portion mounted on a distal end side of said movable portion and a rotatable second joint portion mounted on a proximal end side of said first joint portion and that is similar in shape to said insert slave apparatus with said first and second bending portions bent following rotating operation entered in said first and second joint portions, a treatment master portion which is operated by an operator and following which said treatment slave apparatus is actuated in response to an operation input to said treatment master portion, a coupling for coupling together said movable portion and said treatment master portion wherein said treatment master portion is held for operation so that said movable portion moves through said coupling and said first and second joint portions are rotationally operated.

SUMMARY OF THE INVENTION

The method of controlling a medical master/slave system according to the invention comprising a bendable master apparatus operated by an operator and a bendable slave apparatus inserted through the body includes:

an ordinary actuation mode in which, based on a bending state of the master apparatus, the slave apparatus is actuated such that the slave apparatus becomes similar in actuation to the master apparatus, a reversal actuation mode in which, based on a bending state of the master apparatus, the slave apparatus is actuated in such a way as to be reversed in relation to operation of the master apparatus, and a transition mode for transition between the ordinary actuation mode and the reversal actuation mode.

In the reversal actuation mode of the inventive method of controlling the medical master/slave system, whether or not a reversing portion of the slave apparatus interferes with the rest is determined, and if there is interference, the operation of the master apparatus is restricted.

In the transition mode from the ordinary actuation mode to the reversal actuation mode according to the inventive method of controlling the master/slave system, the master apparatus is actuated to an initial position.

In the transition mode from the reversal actuation to the ordinary actuation mode according to the inventive method of controlling the master/slave system, the master apparatus is actuated in such a way as to become similar to the slave apparatus.

In the inventive method of controlling the medical master/slave system, the ordinary actuation mode makes a transition to the transition mode upon detection of a specific posture taken by the slave apparatus.

In the method of controlling the master/slave system, the ordinary actuation mode presents whether or not a transition to the transition mode is made to an operator who operates the master apparatus upon detection of a specific posture taken by the slave apparatus.

BRIEF DESCRIPTION OF DRAWINGS

FIG. 1 is illustrative in schematic of the construction of the master/slave system 1 according to a specific embodiment of the invention.

FIG. 2 is a block diagram for the master/slave system 1 according to a specific embodiment of the invention.

FIG. 3 is illustrative of the master apparatus 52 in the master/slave system 1 according to a specific embodiment of the invention.

FIG. 4 is illustrative of the slave apparatus 30 in the master/slave system 1 according to a specific embodiment of the invention.

FIG. 5 is illustrative of the master apparatus 52 in the master/slave system 1 according to a specific embodiment of the invention.

FIG. 6 is illustrative of the slave apparatus 30 in the master/slave system 1 according to a specific embodiment of the invention.

FIG. 7 is illustrative of the master apparatus 52 in the master/slave system 1 according to a specific embodiment of the invention.

FIG. 8 is illustrative of the slave apparatus 30 in the master/slave system 1 according to a specific embodiment of the invention.

FIG. 9 is illustrative of an exemplary screen display on the display unit 60 in the master/slave system 1 according to a specific embodiment of the invention.

FIG. 10 is illustrative of an exemplary screen display on the display unit 60 in the master/slave system 1 according to a specific embodiment of the invention.

FIG. 11 is a flowchart for the control processing of the master/slave system 1 according to a specific embodiment of the invention.

FIG. 12 is illustrative of an operation in the reversal mode.

FIG. 13 is illustrative of interferences taking place in the slave apparatus 30 upon the operation shown in FIG. 12.

FIG. 14 is a flowchart for the control processing of the master/slave system 1 according to another specific embodiment of the invention.

FIG. 15 is indicative of definitions of a world coordinate system and a camera coordinate system.

FIG. 16 is a flowchart for the control processing of the master/slave system 1 according to yet another specific embodiment of the invention.

FIG. 17 is a flowchart for the control processing of the master/slave system 1 according to a further specific embodiment of the invention.

DETAILED DESCRIPTION OF THE PREFERRED EMBODIMENTS

Some embodiments of the invention are now explained with reference to the accompanying drawings wherein FIG. 1 is illustrative in schematic of the construction of the master/slave system 1 according to a specific embodiment of the invention; FIG. 2 is a block diagram for the master/slave system 1 according to a specific embodiment of the invention; FIG. 3 is illustrative of the master apparatus 52 in the master/slave system 1 according to a specific embodiment of the invention; and FIG. 4 is illustrative of the master apparatus 30 in the master/slave system 1 according to a specific embodiment of the invention.

The master/slave system 1 according to a specific embodiment of the invention, and how to control the same, is now explained with reference to the drawings.

As shown in FIGS. 1 to 4, the master/slave system 1 according to the embodiment described here is an endoscope system of the master/slave mode comprising a master apparatus 52 in an operating assembly 50 operated by an operator O, an endoscope 4 having a flexible insert assembly 10 to be inserted into the body cavity of a patient P, for instance, a limp internal organ such as the large intestine, a slave apparatus 30 for performing a bending operation at the distal end of the insert assembly 10, a control unit 70 for gaining control of the master apparatus 52 or slave apparatus 30 or a viewing optical system including a lighting portion 17, an imager 40 and so on, and a display unit 60 for displaying images obtained through the endoscope 4.

As shown in FIG. 1, the operating assembly 50 includes the master apparatus 52 attached to an operating mount 51. The master apparatus 52 has a multi-joint structure. The master apparatus 52 is provided to perform the bending operation of the slave apparatus 30 at the distal end of the insert assembly 10.

As shown in FIG. 2, the endoscope 4 includes a viewing optical system comprising the lighting portion 17, imager 40 and so on for obtaining in-vivo images at the rigid distal-end portion 11 of the distal end of the slave apparatus 30. Images obtained through the viewing optical system are processed within the control unit 70 to display them on the display unit 60.

The control unit 70 is constructed of a logic element, a memory, a control program, and so on. The control unit 70 drives a bending-motion motor (not shown) pursuant to an operational instruction from the master apparatus 52 to pull the proper operating wire (not shown) for bending of the slave apparatus 30.

As shown in FIGS. 1 to 4, the endoscope 4 according to the embodiment described here comprises the insert assembly 10 inserted in the body, a treatment tool 39 and the imager 40 located at the rigid distal-end portion 11 positioned at the distal end of the insert assembly 10, the operating assembly 50 operated by the operator O such as a surgeon to produce out an operational instruction (instruction), the display unit 60 for displaying images obtained through the imager 40, and the control unit 70 for gaining control of the insert assembly 10 pursuant to the operational instruction.

The insert assembly 10 is a so-called flexible insert assembly that, as shown in FIG. 4, includes a rigid distal-end portion 11, a slave apparatus 30 located on a proximal end side with respect to the rigid distal-end portion 11 in such a way as to be bendable, and a flexible tubular portion 13 located on a proximal end side with respect to the slave apparatus 30.

The rigid distal-end portion 11 is formed of a transparent member transparent to light emitted out of a lighting portion 17 such as an LED. The rigid distal-end portion 11 is less bendable than the slave apparatus 30. This rigid distal-end portion 11 is provided with a treatment tool 39 such as an electrical knife in such a way as to be inserted through it.

The imager 40 has a built-in imaging device (not shown) such as a CCD. The imaging device 41 is capable of acquiring images within a range of visual field, and then converting them into signals to be sent out to the control unit 70.

The slave apparatus 30 used may have a configuration well known in the art. Although not illustrated, the slave apparatus 30 comprises a plurality of joint rings connected together in such a way as to be mutually rotatable and arranged in an axial direction of the insert assembly 10. The distal one of such joint rings is connected with the distal ends of four operating wires (not shown) at an equiangular interval around the axis of the insert assembly 10. The operating wires are each connected at the proximal end to a slave driver 32 (see FIG. 2) such as a bending-motion motor mounted at the proximal end of the insert assembly 10. The proximal ends of the operating wires are pulled by the slave driver 32 to flex, viz., bend the slave apparatus 30 in any desired bow direction. The control unit 70 is also designed to have a grip of the bending state of the slave apparatus 30 by a slave detector portion 31 (hereinafter called the slave detector).

As illustrated in FIGS. 1 and 3, the operating assembly 50 includes a master apparatus 52, a mode transition button 55, etc. mounted on an operating mount 51. The master apparatus 52 is of a multi-joint structure. The master apparatus 52 is provided to bend the slave apparatus 30 in the insert assembly 10.

The master apparatus 52 is provided with a master detector portion 53 by which the bending state of the master apparatus 52 may be detected. In turn, the master apparatus 52 produces out an operational instruction to the control unit 70 upon operated. Thus, the master apparatus 52 may produce out an operational instruction to operate the slave apparatus 30 via the control unit 70. In the embodiment described here, the control unit 70 may basically perform control such that the bending state of the master apparatus 52 becomes similar to that of the slave apparatus 30. For instance, as the master apparatus 52 is operated as shown in FIG. 5, it causes the slave apparatus 30 to be driven as shown in FIG. 6.

The bending state of the master apparatus 52 may also be controlled by a master driver portion 54 (hereinafter called the master driver 54) actuated in response to a control signal from the control unit 70

The control unit 70 is designed to generate an instruction signal for driving a slave driver portion 32 (hereinafter called the slave driver 32) in response to an operational signal from the master apparatus 52. That is, the control unit 70 calculates out an amount of movement within a certain time of the master apparatus 52 on the proximal end side of the insert assembly 10 to send such an instruction signal as to achieve that amount of movement to the slave driver 32.

When the slave apparatus 30 is used while folded back, there is a problem with the operability of the system, because the direction of operation of the master apparatus 52 differs from the direction of movement of an endoscopic screen display.

Referring here to FIGS. 9 and 10, there is an exemplary screen display on the display unit 60 in the master/slave system 1 according to the embodiment described here. For instance when the master apparatus 52 is operated as shown in FIG. 5 while the slave apparatus 30 is not folded back as shown in FIG. 6, the direction of operation of the master apparatus 52 operated by the operator is the same as the direction of movement of a screen display on the display unit 60, as shown in FIG. 9.

When the master apparatus 52 is operated as shown in FIG. 7 while the slave apparatus 30 is folded back as shown in FIG. 8, on the other hand, the direction of operation of the master apparatus 52 by the operator differs from the direction of movement of a screen display on the display unit 60 as shown in FIG. 10, resulting in poor operability.

Such an operability problem may be solved by the inventive master/slave system 1 that comprises not only an ordinary actuation mode in which the slave apparatus 30 is actuated in such a way as to be similar to the master apparatus 52 but also a reversal actuation mode in which the slave apparatus 30 is actuated in such a way as to be reversed relative to the master apparatus 52.

The mode transition button 55 on the operating assembly 50 enables the operator to give a selective instruction to the control unit 70 as to the transition from the ordinary actuation mode to the reversal actuation mode, or from the reversal actuation mode to the ordinary actuation mode.

Reference is now made to an algorithm for the intra-mode transition processing in the inventive master/slave system 1 configured as described above.

FIG. 11 is a flowchart for the control processing of the master/slave system 1 described here. Note here that this flowchart is one example of the control processing algorithm; other algorithms may be used, too, without departing from the purport of the invention.

The control process gets started in Step S100, and then goes to Step S101 in which a command value is entered in the slave driver on the basis of a bending state of the master apparatus 52 detected by the detector such that the slave apparatus 30 becomes similar to the master apparatus 52 (ordinary actuation mode).

In Step S102, whether or not the mode transition button 55 is pressed down is determined. If the mode transition button 55 is here found to be pressed down, the control processing then goes to the next step in which the respective steps in the transition mode are executed.

In the transition from the ordinary actuation mode to the reversal actuation mode, the driving of the slave apparatus 30 is stopped in Step S103, and the master apparatus 52 is placed in an initial state in Step S104. Note here that the "initial state of the master apparatus 52" means that the master apparatus 52 is in a neutral state or in such a state as shown in FIG. 3.

Then, in Step S105, on the basis of the bending state of the master apparatus 52 detected by the master detector 53, a command value is entered into the slave driver such that the slave apparatus 30 is reversed relative to the master apparatus 52 (reversal actuation mode). Note here that "controlling the slave apparatus 30 in such a way as to be reversed relative to the master apparatus 52" means that a command value with the plus and minus of the ordinary command value being reversed is entered into the slave driver 32. Such a reversal actuation mode makes the direction of operation of the master apparatus 52 identical with the direction of movement of an endoscope screen display, resulting in improved operability.

In the reversal actuation mode, the slave and master apparatuses 30 and 52 do not necessarily coincide in terms of spatial position as shown in FIGS. 11 and 12. For this reason, it is assumed that although depending on the operation of the master apparatus, there may be interference occurring where the reversing portion of the slave apparatus 30 comes in collision with the rest.

In the reversal actuation mode, whether or not such interference as mentioned above occurs is determined. If the interference is found to occur, the control processing then goes to Step S107 in which the operation of the master apparatus 52 is restricted by the master driver 54. Note here that detection of such interference as described above and control of restriction on the operation of the master apparatus 52 are left out of the flowchart.

It is here to be noted that whether or not such interference as collision of the slave apparatus 30 with itself occurs may be determined through a detection value obtained by a contact sensor attached to the slave apparatus 30 or, alternatively, by the magnitude of a difference between the command value to the master apparatus 52 and the amount of movement of the slave apparatus 30. The restriction imposed on the operation of the master apparatus 52 may be notified to the operator by applying an output on the master driver 54 on the master apparatus 52 side to control the slave apparatus 30 such that it does not move in such a direction as to cause the slave apparatus 30 to interfere with itself.

In Step S106, whether or not the mode transition button 55 is pressed down is determined. If the mode transition button 55 is here found to be pressed down, the control processing then goes to the next step for execution of the respective steps of the transition mode.

Upon transition from the reversal actuation mode to the ordinary actuation mode, the driving of the slave apparatus 30 is stopped in Step S108, and in Step S109, the master apparatus 52 is made similar to the slave apparatus 30 by the master driver 54. After execution of the respective steps of such a transition mode as described above, the control processing returns back to Step S101 for execution of the ordinary actuation mode.

The inventive master/slave system 1, and how to control the same, as described above, includes the reversal actuation mode in which, based on the bending state of the master apparatus 52 detected by the master detector 53, the command value is entered in the slave driver 32 such that the slave apparatus 30 is reversed relative to the master apparatus 52. Thus, the inventive master/slave system, and the inventive method of controlling the same ensures that the operability of the system is improved upon the folding-back of the slave apparatus 30.

Another embodiment of the invention is now explained. While the intra-mode changeover is manually made, it is to be understood that the intra-mode changeover is automatically made. For the determination of the intra-mode changeover, the world coordinate system ($X_w$, $Y_w$, $Z_w$) with reference to the flexible tubular portion 13 is introduced together with the camera coordinate system ($X_i$, $Y_i$, $Z_i$) with reference to the imager 40.

FIG. 14 is a flowchart for the control processing of the master/slave system 1 according to another embodiment of the invention. Note here that this flowchart is one example of the algorithm for the control processing; other algorithms may be used, too, without departing from the purport of the invention.

The control processing gets started in Step S200, and then goes to Step S201 in which, based on a bending state of the master apparatus 52 detected by the detector, a command value is entered in the slave driver such that the slave apparatus 30 becomes similar to the master apparatus 52 (ordinary actuation mode).

In Step S202, whether or not the angle of the $Z_i$ axis forming with the $Z_w$ axis is greater than 90° is determined. If the determination in this step S202 is YES indicating the transition to the reversal actuation mode, the control processing then goes to Step S203 for execution of the respective steps of the transition mode.

While the two coordinate systems are introduced for the mode changeover determination in the embodiment described here, it is understood that the mode changeover determination may be made on the basis of the posture of the distal end figured out by an acceleration sensor attached to the distal end of the master apparatus 52 or the slave apparatus 30.

In the transition mode from the ordinary actuation mode to the reversal actuation mode, the driving of the slave apparatus 30 is stopped in Step S203, and the master apparatus 52 is placed in an initial state in Step S204. Note here that the "initial state of the master apparatus 52" means that the master apparatus 52 is in a neutral state or in such a state as shown in FIG. 3.

Then, in Step S205, on the basis of the bending state of the master apparatus 52 detected by the master detector 53, a command value is entered in the slave driver such that the slave apparatus 30 is reversed relative to the master apparatus 52 (reversal actuation mode). Note here that "controlling the slave apparatus 30 in such a way as to be reversed relative to the master apparatus 52" means that a command value with the plus and minus of the ordinary command value being reversed is entered in the slave driver 32. Such a reversal actuation mode makes the direction of operation of the master apparatus 52 identical with the direction of movement of an endoscopic screen display, resulting in improved operability.

In the reversal actuation mode, the slave and master apparatuses 30 and 52 do not necessarily coincide in terms of spatial position as shown in FIGS. 11 and 12. For this reason, it is assumed that although depending on the operation of the master apparatus, there may be interference occurring where the reversing portion of the slave apparatus 30 comes in collision with the rest.

In the reversal actuation mode, whether or not such interference as mentioned above occurs is determined. If the interference is found to occur, the control processing then goes to Step S207 in which the operation of the master apparatus 52 is restricted by the master driver 54. Note here that detection of such interference as described above and control of restriction on the operation of the master apparatus 52 are left out of the flowchart.

It is here to be noted that whether or not such interference as collision of the slave apparatus 30 with itself occurs may be determined through a detection value obtained by a contact sensor attached to the slave sensor 30 or, alternatively, by the magnitude of a difference between the command value to the master apparatus 52 and the amount of movement of the slave apparatus 30. The restriction imposed on the operation of the master apparatus 52 may be notified to the operator by applying an output on the master driver 54 on the master apparatus 52 side to control the slave apparatus 30 such that it does not move in such a direction as to cause the slave apparatus 30 to interfere with itself.

In Step S206, whether or not the angle of $Z_i$ axis to the $Z_w$ axis is greater than 90° is determined. If the determination in this step S206 is NO indicating the transition to the ordinary actuation mode, the control processing then goes to Step S208 for execution of the respective steps of the transition mode.

In the transition mode from the reversal actuation mode to the ordinary actuation mode, the driving of the slave apparatus 30 is stopped in Step S208, and in Step S209, the master apparatus 52 is made similar to the slave apparatus 30 by the master driver 54. After execution of the respective steps of such a transition mode as described above, the control processing returns back to Step S201 for execution of the ordinary actuation mode.

The master/slave system, and the method of controlling the same, according to such another embodiment as described above, has those similar to the advantages of the first embodiment, and enables automatic mode transition, resulting in more improved operability.

Yet another embodiment of the invention is now explained. In the second embodiment of the invention, the intra-mode changeover is automatically made; however, in some possible cases, there may be no need for the operator to make a changeover to the reversal actuation mode. In the embodiment described here, therefore, the operator is urged to make a changeover from the ordinary actuation mode to the reversal actuation mode upon detection of a specific posture taken by the slave apparatus 30. In other words, whether or not the mode changeover is actually made is left to the operator.

FIG. 16 is a flowchart for the control processing of the master/slave system 1 according to yet another embodiment of the invention. Note here that this flowchart is one example of the algorithm for the control process; other algorithms may be used, too, without departing from the purport of the invention.

The control processing gets started in Step S300, and then goes to Step S301 in which, based on a bending state of the master apparatus 52 detected by the detector, a command value is entered in the slave driver such that the slave apparatus 30 becomes similar to the master apparatus 52 (ordinary actuation mode).

In Step S302, whether or not the angle of the $Z_i$ axis forming with the $Z_w$ axis is greater than 90° is determined. If the determination in this Step S302 is YES, the control process then goes to Step S303 urging the operator to select any one of the ordinary or the reversal actuation mode on the display unit 60.

While the two coordinate systems are introduced for the mode changeover determination in the embodiment described here, it is understood that the mode changeover determination may be made on the basis of the posture of the distal end figured out by an acceleration sensor attached to the distal end of the master apparatus 52 or the slave apparatus 30.

In the embodiment described here, a screen display on the display unit 60 is used as the means for urging the operator to make the transition from the ordinary to the reversal actuation mode; however, it is to be noted that notification by way of sounds or tactile senses may be used as the means for urging the operator to make the transition from the ordinary to the reversal actuation mode.

In Step S304, whether or not the operator selects the reversal actuation mode is determined. If the determination in Step S304 is NO, the control process then goes to Step S301 for keeping on with the ordinary actuation mode. If the determination in Step S304 is YES, on the other hand, the control process then goes to Step S305 for a preparation to the transition to the reversal actuation mode, in which the respective steps of the transition mode are executed.

In the transition mode from the ordinary actuation mode to the reversal actuation mode, the driving of the slave apparatus 30 is stopped in Step S305, and the master apparatus 52 is placed in an initial state in Step S306. Note here that the "initial state of the master apparatus 52" means that the master apparatus 52 is in a neutral state or in such a state as shown in FIG. 3.

Then, in Step S307, on the basis of the bending state of the master apparatus 52 detected by the master detector 53, a command value is entered in the slave driver such that the slave apparatus 30 is reversed relative to the master apparatus 52 (reversal actuation mode). Note here that "controlling the slave apparatus 30 in such a way as to be reversed relative to the master apparatus 52" means that a command value with the plus and minus of the ordinary command value being reversed is entered in the slave driver 32. Such a reversal actuation mode makes the direction of operation of the master apparatus 52 identical with the direction of movement of an endoscopic screen display, resulting in improved operability.

In the reversal actuation mode, the slave and master apparatuses 30 and 52 do not necessarily coincide in terms of spatial position as shown in FIGS. 11 and 12. For this reason, it is assumed that although depending on the operation of the master apparatus, there may be interference occurring where the reversing portion of the slave apparatus 30 comes in collision with the rest.

In the reversal actuation mode, whether or not such interference as mentioned above occurs is determined. If the interference is found to occur, the control processing then goes to Step S307 in which the operation of the master apparatus 52 is restricted by the master driver 54. Note here that detection of such interference as described above and control of restriction on the operation of the master apparatus 52 are left out of the flowchart.

It is here to be noted that whether or not such interference as collision of the slave apparatus 30 with itself occurs may be determined through a detection value obtained by a contact sensor attached to the slave sensor 30 or, alternatively, by the magnitude of a difference between the command value to the master apparatus 52 and the amount of movement of the slave apparatus 30. The restriction imposed on the operation of the master apparatus 52 may be notified to the operator by applying an output on the master driver 54 on the master apparatus 52 side to control the slave apparatus 30 such that it does not move in such a direction as to cause the slave apparatus 30 to interfere with itself.

In Step S308, whether or not the angle of the $Z_i$ axis forming with the $Z_w$ axis is greater than 90° is determined.

If the determination in this step S308 is NO indicating the transition to the ordinary actuation mode, the control processing then goes to Step S309 for execution of the respective steps of the transition mode.

In the transition mode from the reversal actuation mode to the ordinary actuation mode, the driving of the slave apparatus 30 is stopped in Step S309, and in Step S310, the master apparatus 52 is made similar to the slave apparatus 30 by the master driver 54. After execution of the respective steps of such a transition mode as described above, the control processing returns back to Step S301 for execution of the ordinary actuation mode.

The master/slave system, and the process of controlling it, according to such another embodiment as described above, produces those similar to the advantages of the former embodiment, and makes it possible for the operator to select mode transitions of her or his own choice, resulting in more improved operability.

A further embodiment of the invention is now explained. In the embodiments described so far herein, the master apparatus 52 is designed to return back to the initial state in the transition mode from the ordinary to the reversal actuation mode. In the embodiment described here, however, such resumption of the master apparatus 52 in the initial state is dispensed with.

FIG. 17 is a flowchart for the control processing of the master/slave system 1 according to a further embodiment of the invention. Note here that this flowchart is one example of the algorithm for the control processing; other algorithms may be used, too, without departing from the purport of the invention.

The control processing gets started in Step S400, and then goes to Step S401 in which, based on a bending state of the master apparatus 52 detected by the detector, a command value is entered in the slave driver such that the slave apparatus 30 becomes similar to the master apparatus 52 (ordinary actuation mode).

In Step S402, whether or not the mode transition button 55 is pressed down is determined. If the mode transition button 55 is here found to be depressed, the control processing then goes to Step S403.

Then, in Step S405, on the basis of a bending state of the master apparatus 52 detected by the master detector 53, a command value is entered in the slave driver such that the slave apparatus 30 is reversed relative to the master apparatus 52 (reversal actuation mode). Note here that "controlling the slave apparatus 30 in such a way as to be reversed in relation to the master apparatus 52" means that a command value with the plus and minus of the ordinary command value being reversed is entered in the slave driver 32. Such a reversal actuation mode makes the direction of operation of the master apparatus 52 identical with the direction of movement of a screen display of endoscopic images, resulting in improved operability.

In the reversal actuation mode, the slave and master apparatuses 30 and 52 do not necessarily coincide in terms of spatial position. For this reason, it is assumed that although depending on the operation of the master apparatus, there may be interference occurring where the reversing portion of the slave apparatus 30 comes in collision with the rest.

In the reversal actuation mode, whether or not such interference as mentioned above occurs is determined. If the interference is found to occur, the control process then goes to Step S407 in which the operation of the master apparatus 52 is restricted by the master driver 54. Note here that detection of such interference as described above and control of restriction on the operation of the master apparatus 52 are left out of the flowchart.

It is here to be noted that whether or not such interference as collision of the slave apparatus 30 with itself occurs may be determined through a detection value obtained by a contact sensor attached to the slave sensor 30 or, alternatively, by the magnitude of a difference between the command value for the master apparatus 52 and the amount of movement of the slave apparatus 30. The restriction imposed on the operation of the master apparatus 52 may be notified to the operator by applying an output on the master driver 54 on the master apparatus 52 side to control the slave apparatus 30 such that it does not move in such a direction as to cause the slave apparatus 30 to interfere with itself.

In Step S404, whether or not the mode transition button 55 is pressed down is determined. If the mode transition button 55 is here to be depressed, the control process then goes to the next step for execution of the respective steps of the transition mode.

In the transition from the reversal to the ordinary actuation mode, the driving of the slave apparatus 30 is stopped in Step S405, and in Step S406, the master apparatus 52 is allowed by the master driver 54 to become similar to the slave apparatus 30. After execution of the respective steps of such a transition mode as mentioned above, the control process then goes back to Step S401 for execution of the ordinary actuation mode.

The master/slave system, and the method of controlling the same, according to such fourth embodiment as described above, produces those similar to the advantages of the former embodiments.

REFERENCE SIGNS LIST

1: Mater/slave system
4: Endoscope
10: Insert assembly
11: Rigid distal-end portion
13: Flexible tubular portion
17: Lighting portion
30: Slave apparatus
31: Slave detector portion
32: Slave driver
39: Treatment tool
40: Imager
50: Operating assembly
51: Operating mount
52: Master apparatus
53: Master detector portion
54: Master driver
55: Mode transition button
60: Display unit
70: Control unit
81: Operating table
O: Operator
P: Patient
F: Floor surface

The invention claimed is:
1. A method of controlling a medical master/slave system comprising a bendable master apparatus operated by an operator and a bendable slave apparatus inserted through the body and a control unit for gaining a control of the master apparatus and the slave apparatus, the method comprising:
an ordinary actuation mode configured to:
detect a bending direction of the master apparatus;
calculate a command value of the slave apparatus such that a bending direction of the slave apparatus becomes similar to the bending direction of the master apparatus; and
enter the command value in the slave apparatus so as to actuate the slave apparatus;
a reversal actuation mode configured to:
detect the bending direction of the master apparatus;
calculate the command value of the slave apparatus such that the bending direction of the slave apparatus becomes similar to the bending direction of the master apparatus;
correct the command value by reversing the sign of the command value; and
enter the command value in the slave apparatus so as to actuate the slave apparatus; and
a transition mode configured to:
stop to actuate the slave apparatus; and
transit between the ordinary actuation mode and the reversal actuation mode.

2. The method of controlling the master/slave system as recited in claim 1,
wherein in the reversal actuation mode:
determining whether or not a reversing portion of the slave apparatus collides with a non-reversing portion of the slave apparatus; and
in response to determining that the reversing portion of the slave apparatus collides with the non-reversing portion of the slave apparatus, restricting the operation of the master apparatus.

3. The method of controlling the master/slave system as recited in claim 1,
wherein in the transition mode from the ordinary actuation mode to the reversal actuation mode, the master apparatus is actuated to an initial position.

4. The method of controlling the master/slave system as recited in claim 1,
wherein in the transition mode from the reversal actuation mode to the ordinary actuation mode, the master apparatus is actuated in such a way as to become similar to the slave apparatus.

5. The method of controlling the master/slave system as recited in claim 1,
wherein the ordinary actuation mode makes a transition to the transition mode upon detection of a specific posture taken by the slave apparatus.

6. The method of controlling the master/slave system as recited in claim 1,
wherein the ordinary actuation mode presents whether or not a transition to the transition mode is made to the operator who operates the master apparatus upon detection of a specific posture taken by the slave apparatus.

7. A medical system comprising:
a bendable master apparatus configured to be operated by an operator;
a bendable slave apparatus configured to be inserted through the body;
a control unit configured to control both the master apparatus and the slave apparatus, based on a plurality of modes, wherein the plurality of modes comprises:
an ordinary actuation mode configured that the slave apparatus is actuated such that a bending direction of the slave apparatus becomes similar to a bending direction of the master apparatus;
a reversal actuation mode configured that the slave apparatus is actuated in such a way as to be reversed a bending direction of the slave apparatus relative to a bending direction of the master apparatus; and a transition mode configured to:
   stop to actuate the slave apparatus; and
   in response to transit from the ordinary actuation mode to the reversal actuation mode:
      actuate the master apparatus to an initial position;
   in response to transit from the reversal actuation mode to the ordinary actuation mode:
      actuate the master apparatus so as to be similar to a bending direction of the slave apparatus; and
      restart to actuate the slave apparatus after actuating the master apparatus.

8. The medical system according to claim 7,
wherein in the reversal actuation mode, the control unit is configured to:
   determine whether or not a reversing portion of the slave apparatus collides with a non-reversing portion of the slave apparatus; and
   in response to determining that the reversing portion of the slave apparatus collides with the non-reversing portion of the slave apparatus, restrict the operation of the master apparatus.

9. The method according to claim 1,
wherein a structure of a bendable portion of the master apparatus is substantially the same as a structure of a bendable portion of the slave apparatus.

10. The method according to claim 9,
wherein the initial position is configured that the bendable portion of the master apparatus is not bending.

11. The medical system according to claim 7,
wherein a structure of a bendable portion of the master apparatus is substantially same as a structure of a bendable portion of the slave apparatus.

12. The medical system according to claim 11,
wherein the initial position is configured that the bendable portion of the master apparatus is not bending.

13. The medical system according to claim 7,
wherein the ordinary actuation mode configured to:
   detect a bending direction of the mast apparatus;
   calculate a command value of the slave apparatus such that a bending direction of the slave apparatus becomes similar to the bending direction of the master apparatus;
   enter the command value in the slave apparatus so as to actuate the slave apparatus; and
wherein the reversal actuation mode configured to:
   detect the bending direction of the master apparatus;
   calculate the command value of the slave apparatus such that the bending direction of the slave apparatus becomes similar to the bending direction of the master apparatus;
   correct the command value by reversing the sign of the command value; and
   enter the command value in the slave apparatus so as to actuate the slave apparatus.

* * * * *